United States Patent [19]
Lukic

[11] Patent Number: 5,534,287
[45] Date of Patent: Jul. 9, 1996

[54] METHODS FOR APPLYING AN ELASTIC COATING LAYER ON STENTS

[75] Inventor: Goran Lukic, Bülach, Switzerland

[73] Assignee: Schneider (Europe) A.G., Bulach, Switzerland

[21] Appl. No.: 346,066

[22] Filed: Nov. 29, 1994

Related U.S. Application Data

[62] Division of Ser. No. 173,542, Dec. 22, 1993, abandoned.

[30] Foreign Application Priority Data

Apr. 23, 1993 [EP] European Pat. Off. .............. 93106646

[51] Int. Cl.⁶ .............................. B05D 1/28; B05D 3/02; B29C 65/00; B32B 31/00
[52] U.S. Cl. .................. 427/2.25; 427/2.28; 427/178; 427/177; 156/294; 156/303.1
[58] Field of Search .................... 427/2.25, 2.28, 427/178, 2.24, 177, 11; 156/294, 303.1

[56] References Cited

U.S. PATENT DOCUMENTS

| | | |
|---|---|---|
| 4,140,126 | 2/1979 | Choudhury . |
| 4,331,727 | 5/1982 | Maas ......................................... 427/177 |
| 4,356,218 | 10/1982 | Chia et al. ................................ 427/429 |
| 4,536,179 | 8/1985 | Anderson et al. ........................ 427/2.3 |
| 4,553,545 | 11/1985 | Maass et al. . |
| 4,572,186 | 2/1986 | Gould et al. . |
| 4,580,568 | 4/1986 | Gianturco . |
| 4,605,406 | 8/1986 | Cahalan et al. ........................ 427/2.25 |
| 4,649,922 | 3/1987 | Wiktor . |
| 4,655,771 | 4/1987 | Wallsten . |
| 4,665,918 | 5/1987 | Garza et al. . |
| 4,681,110 | 7/1987 | Wiktor . |
| 4,699,611 | 10/1987 | Bowden . |
| 4,710,181 | 12/1987 | Fuqua ....................................... 604/280 |
| 4,723,549 | 2/1988 | Wholey et al. . |
| 4,732,152 | 3/1988 | Wallsten et al. . |
| 4,733,665 | 3/1988 | Palmaz . |
| 4,768,507 | 9/1988 | Fischell et al. . |
| 4,793,348 | 12/1988 | Palmaz . |
| 4,800,882 | 1/1989 | Gianturco . |
| 4,830,003 | 5/1989 | Wolff et al. . |
| 4,848,343 | 7/1989 | Wallsten et al. . |

(List continued on next page.)

FOREIGN PATENT DOCUMENTS

| | | |
|---|---|---|
| 0183372 | 6/1986 | European Pat. Off. . |
| 3918736A1 | 12/1990 | Germany . |
| 1205743 | 9/1970 | United Kingdom . |
| 1565828 | 4/1980 | United Kingdom . |
| 9317636 | 9/1993 | WIPO . |

OTHER PUBLICATIONS

Derwent Abstract 48501 of DT 3325346, Jan. 1985.
Binmoeller, K. F., et al., "Silicone–Covered Expandable Metallic Stents in the Esophagus: An Experimental Study", pp. 416–420, 1992 Endoscopy. (no month available).
Fleischer, David E., et al., "A New Coated Self–Expanding Metal Stent for Malignant Esophageal Strictures", pp. 494–496, 1992, Gastrointestinal Endoscopy. (Jul.).
Pilkington, Theo C., Duke–North Carolina NSF/ERC for Emerging Cardiovascular Technologies Annual Report, Jul. 29, 1988.
Domschke, W., et al., "Self–Expanding Mesh Stent for Esophageal Cancer Stenosis", pp. 134–136, 1990 Endoscopy. (No Month).
Song, Ho–Young et al., "Esophagogastric Neoplasms: Palliation with a Modified Gianturco Stent", pp. 349–354, 1991 Radiology. (Aug).

*Primary Examiner*—Diana Dudash
*Attorney, Agent, or Firm*—Peter C. Richardson; Lawrence C. Akers; Philip C. Strassburger

[57] ABSTRACT

The coated stent comprises a cylindrical wall formed by meshed wires and a covering layer of elastic material extending on a portion of its length, with an outer surface, and totally embracing the wire mesh.

Method of coating the stent using a lifting medium and then an elastomeric composition dissolved in solvent are disclosed.

5 Claims, 1 Drawing Sheet

U.S. PATENT DOCUMENTS

| | | | |
|---|---|---|---|
| 4,850,999 | 7/1989 | Planck . | |
| 4,856,516 | 8/1989 | Hillstead . | |
| 4,876,109 | 10/1989 | Mayer et al. | 427/2.28 |
| 4,878,906 | 11/1989 | Lindemann et al. . | |
| 4,886,062 | 12/1989 | Wiktor . | |
| 4,921,484 | 5/1990 | Hillstead . | |
| 4,954,126 | 9/1990 | Wallsten . | |
| 5,015,253 | 5/1991 | MacGregor | 623/1 |
| 5,026,377 | 5/1991 | Burton et al. . | |
| 5,026,607 | 6/1991 | Kiezulas | 427/2.1 |
| 5,061,275 | 10/1991 | Wallsten et al. . | |
| 5,064,435 | 11/1991 | Porter . | |
| 5,071,407 | 12/1991 | Termin et al. . | |
| 5,089,006 | 2/1992 | Stiles . | |
| 5,100,429 | 3/1992 | Sinofsky et al. | 606/195 |
| 5,108,416 | 4/1992 | Ryan et al. . | |
| 5,112,900 | 5/1992 | Buddenhagen et al. . | |
| 5,158,548 | 10/1992 | Lau et al. . | |
| 5,171,262 | 12/1992 | MacGregor . | |
| 5,211,658 | 5/1993 | Clouse . | |
| 5,217,026 | 6/1993 | Stoy et al. | 427/336 |
| 5,246,452 | 9/1993 | Sinnot | 623/1 |
| 5,272,012 | 12/1993 | Opolski | 427/2.1 |
| 5,282,823 | 2/1994 | Schwartz et al. | 606/198 |
| 5,288,359 | 2/1994 | Stobbie IV et al. | 156/294 |
| 5,330,449 | 7/1994 | Prichard et al. | 156/294 |
| 5,336,351 | 8/1994 | Meyers | 156/294 |
| 5,338,312 | 8/1994 | Montgomery | 427/2.3 |
| 5,356,433 | 10/1994 | Rowland et al. | 427/2.24 |
| 5,382,234 | 1/1995 | Cornelius et al. | 604/282 |
| 5,389,106 | 2/1995 | Tower | 606/198 |
| 5,395,349 | 3/1995 | Quiachon et al. | 604/248 |
| 5,421,826 | 6/1995 | Crocker et al. | 604/282 |

METHODS FOR APPLYING AN ELASTIC COATING LAYER ON STENTS

This is a division of application Ser. No. 08/173,542, filed on Dec. 22, 1993, now abandoned.

BACKGROUND OF THE INVENTION

This invention relates to a stent with a discontinuous expandable wall comprising on at least a portion of its length a continuous covering layer of elastic material with an outer surface surrounding the discontinuous wall. This invention also relates to methods for applying such a layer on a stent.

The discontinuous walls of stents, such as for instance the macroporous walls formed by a deformable wire mesh allowing diametral retraction for introduction of the stent into air or food pipes and expansion therein for dilatation, or repair, or bridging of said pipes, have the disadvantage that they permit ingrowth of tumors and other rapid growth cells through the wire mesh or discontinuous wall, with the resulting risk of stent occlusion.

For preventing ingrowth of cells through the stent, the document DE-3918736-A1 describes an expandable metallic stent with an inner Teflon® tube affixed to the stent by suture or pressure, or an inner tube and an outer tube, both of Teflon®, connected pouch like to each other. At least in case of degradation of the inner tube, there will be a strong risk of having flaps from the inner tube occluding the vessel, or migration of the inner tube with respect to the stent and a further risk of occlusion of the vessel. Furthermore, the absence of resiliency of Teflon® does not allow constriction and expansion of the stent without additional place consuming measures such as zig-zag folds of the Teflon® tubes.

The document "Endoscopy 1992:416–420" also describes an expandable metallic stent for preventing ingrowth of malignant structures. This stent, formed by an expandable wire mesh, is covered by a silicone membrane or skirt which surrounds a portion of its length.

This membrane or skirt is secured around the stent by suture of its ends to the wire mesh, and, in situ, the membrane is thus radially held in place between the stent wall and vessel wall. To have the membrane or skirt positioned between the stent wall and vessel wall is advantageous in case of degradation of the membrane. However, such a coverage of the stent is far from being effortless and mostly will have to be done by hand, which will require skills. In addition, it is limited to certain types of materials and it may prove fragile, being possible to have the membrane or skirt getting loose from the wire mesh, which may allow relative movement between the membrane and the stent, with the resulting risk of occluding the vessel.

The object of this invention is to avoid the aforesaid drawbacks.

To this effect, the stent and methods in accordance with the invention comply with the definitions given in the claims.

In that way, the continuous covering layer is closely bound to the discontinuous structure which it covers and there is definitely no risk of separation therebetween. And even in the case of a strong degradation of the covering layer in course of time, there cannot be any migration of the covering layer with respect to the discontinuous wall of the stent because of the aforesaid intimal interconnection. Furthermore, the liaison of the covering layer with the discontinuous wall of the stent eliminates any delicate, time and skill consuming efforts and allows coating of any kind of discontinuous expandable stent wall.

In sum, the present invention relates to a stent with a discontinuous expandable wall and a continuous covering layer of elastic material surrounding the discontinuous wall. The continuous covering layer of elastic material is adhered to the discontinuous wall so it is intimately united with said discontinuous wall. The continuous covering layer of elastic material may extend at least partly radially within the discontinuous wall of the stent, and may extend around and inside the discontinuous wall of the stent. The continuous covering layer may be adhered to the discontinuous wall by means of a binder, or it may be heat adhered or chemically bonded to the discontinuous wall. The continuous covering layer may be adhered to the discontinuous wall by radial pressure of the discontinuous wall against the continuous covering layer. The continuous covering layer may have a structured surface towards the discontinuous wall, wherein the continuous covering layer is adhered to the discontinuous wall as a result of said structured surface.

The present invention also relates to a method for applying a covering layer to a stent by radially contracting the stent; inserting at least a portion of the contracted stent into a tube the inner surface of which has been previously done over with a lifting medium; allowing the stent to radially expand in the tube; wetting the assembly tube plus stent with an elastomeric polymerisable composition dissolved in a sufficient amount of solvent to permit wet forming; evaporating the solvent; polymerizing the elastomeric composition in the tube; and taking the layer covered portion of the stent out of the tube. The tube, the inner surface of which has been done over with a lifting medium, may be first wetted along with the elastomeric composition added with solvent. The solvent may be evaporated before the step of insertion of the stent into the tube.

The present invention also relates to a method for applying a covering layer to a stent by doing over a roll on surface with a lifting medium; coating said roll on surface with an elastomeric polymerisable composition dissolved in a sufficient amount of solvent to permit contact forming; rolling at least a portion of the stent in expanded condition on said coated roll on surface; withdrawing the stent from the roll on surface; evaporating the solvent; and polymerizing the elastomeric composition adhered by contact on said portion of the stent.

The present invention also relates to a method for applying a covering layer to a stent by forming a tube of predetermined length with an elastomeric polymerisable composition; radially contracting the stent; inserting into the tube a portion of the stent corresponding to said predetermined length of the tube; allowing the stent to radially expand in the tube, and welding the surfaces of contact between the stent and the tube.

The present invention also relates to a method for applying a covering layer to a stent by forming a tube of predetermined length with an elastomeric polymerisable composition; coating the inside of the tube with an adhesive medium; radially contracting the stent; inserting into the tube a portion of the stent corresponding to said predetermined length of the tube; allowing the stent to radially expand in the tube; and allowing the adhesive medium to cure.

The present invention also relates to a method for applying a covering layer to a stent by forming a tube of predetermined length with an elastomeric polymerisable composition; coating the inside of the tube with an elastomeric polymerisable composition dissolved in a sufficient amount of solvent to permit contact forming; radially contracting the stent; inserting into the tube a portion of the stent corresponding to said predetermined length of the tube; allowing the stent to radially expand in the tube; evaporating the solvent; and polymerizing the elastomeric composition adhered by contact to the tube and to the stent.

BRIEF DESCRIPTION OF THE DRAWINGS

The invention will now be described more particularly with references to the accompanying drawings which show, by way of example only, one embodiment of the invention.

In the drawings.

DETAILED DESCRIPTION OF A PREFERRED EMBODIMENT

Figure 1:
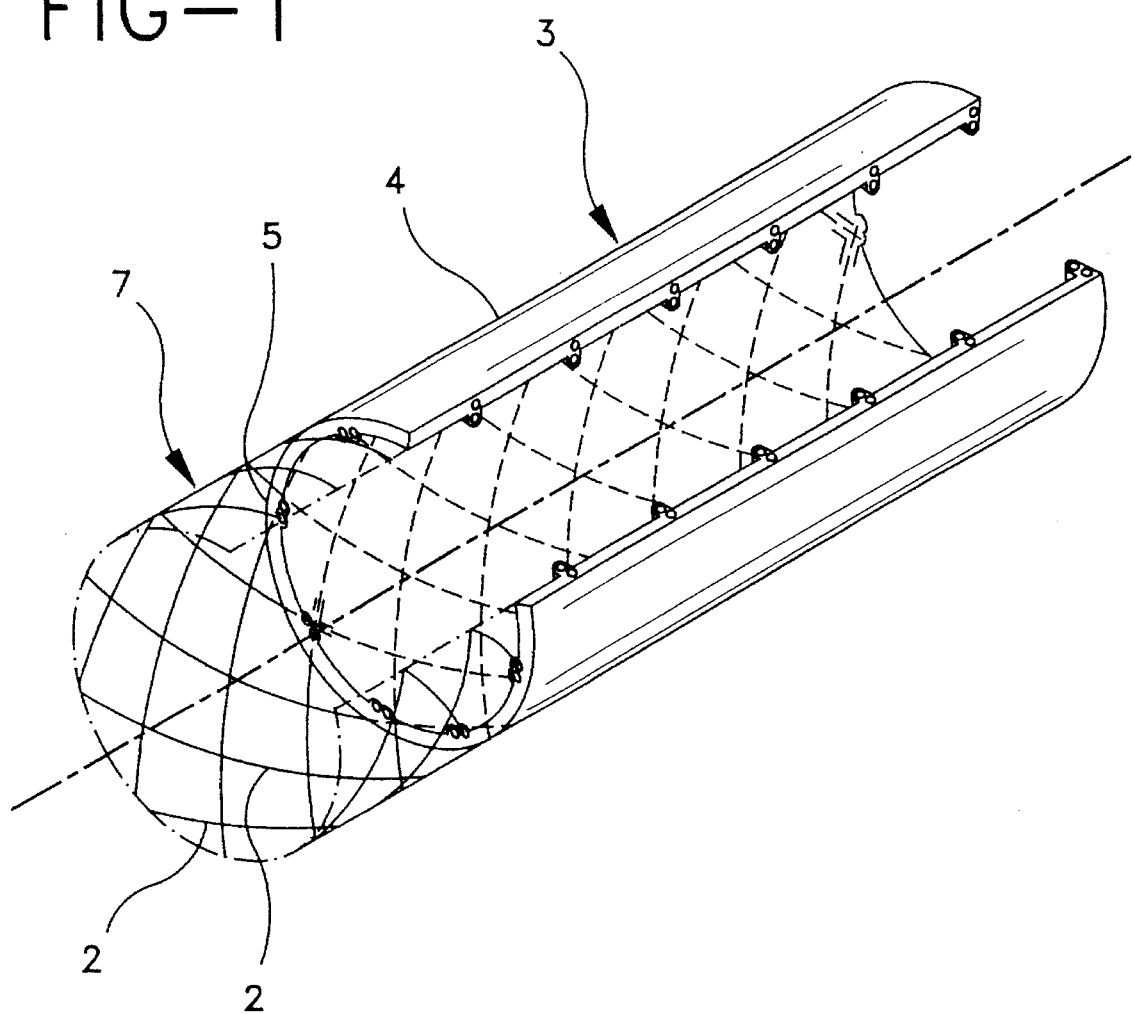
FIG. 1 is a perspective view of a quarter cut along the longitudinal axis of the exemplified embodiment.

The stent shown in FIG. 1 is an expandable stent of which the wall (1), for instance cylindrical, is formed by meshed wires (2) of stainless steel, plastics or hybrid materials as plastics and carbon fiber.

The wall (1) comprises, on a portion of its length, a covering layer (3) made of an elastomeric biocompatible composition such as, for instance, the elastomeric polymerisable composition described in U.S. Pat. No. 5,112,900. The outer face (4) of layer (3) forms a surrounding surface, and layer (3) extends around and inside the discontinuous structure of the stent in order to totally embrace and intimately unite with any material part of the meshed wires (2) which constitute said discontinuous structure.

On FIG. 1, the left front face (5) of the covering layer (3) is shown in an area of wall (1) where the wires (2) do not cross each other; on the contrary, the quarter cut along the longitudinal axis is shown in an area where the wires (2) cross and overlap each other.

Figure 2:
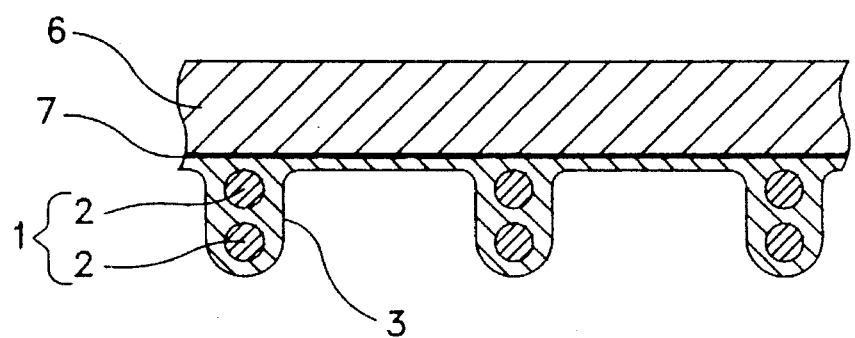
FIG. 2 is an enlarged view of an axial cut of a portion of its wall during a procedure for applying the covering layer.

A portion of the stent wall (1) is shown on FIG. 2 with its covering layer (3), the stent wall (1) being shown in an area where its wires (2) overlap each other, and the stent being inserted in a tube (6) the inner surface of which is coated with a lifting medium (7) as described in detail hereafter in connection with a procedure for applying the covering layer to the stent.

In order to apply the covering layer (3) on the stent, the deformable wall (1) of the stent is radially contracted and the portion thereof which has to be coated is inserted into the tube (6) the inner surface of which has been previously done over with a lifting medium (7) such as for instance "Teflon®" in order to avoid adherence to the elastomeric composition forming the covering layer (3). The contracted stent is allowed to expand radially in the tube (6) and the assembly of the tube and stent is wetted with the elastomeric polymerisable composition dissolved in a sufficient amount of solvent to permit wet forming of a continuous covering layer around the totality of the discontinuous wall of the stent formed by the wire mesh inside the tube (6). The solvent is evaporated and the elastomeric composition is then polymerized in the tube and the layer covered stent portion is taken out of the tube.

In that way, the shaping and liaison of the covering layer with the discontinuous wall of the stent is obtained automatically by mass polymerization of the elastomeric composition wholly surrounding the structure of such a wall inside the tube moulding its outer surface.

Of course, the discontinuous wall of the stent may also be covered with the continuous covering layer all over its length, in which case the stent will be fully inserted into the tube for the dip forming process. In addition, the invention is not limited to the embodiment shown, being applicable to any kind of expandable stent having a discontinuous wall.

The thickness of the covering layer may be advantageously selected as a function of the quantity of solvent added to the elastomeric composition, before polymerization and within the limits of a fluidity sufficient to allow wetting.

As a variant, it is also possible to obtain a greater thickness of the portions of the covering layer which are located at the outside of the discontinuous wall of the stent and between the mesh or elements thereof. To this effect, the tube (6) done over with the lifting medium is first wetted alone with the elastomeric composition previously added with an appropriate amount of solvent. The solvent is evaporated and the stent is then radially contracted for insertion into the tube and the procedure follows as outlined hereinbefore.

According to a variant, not shown, the covering layer of elastic material needs not to integrally embrace the discontinuous structure of the stent, being sufficient that only a part of the thickness of the structure be covered by the elastic material, in case of the example shown in FIG. 1, only a radial portion of the wires (2).

According to further variants, also not shown, the elastic covering may be achieved by surface adhesion forces or through use of a binder.

Accordingly, a variant method provides for doing over a roll on surface with a lifting medium and coating said roll on surface with an elastomeric polymerisable composition dissolved in a sufficient amount of solvent to permit contact forming, such an elastomeric composition being, for instance, the composition described in U.S. Pat. No. 5,112,900. An appropriate portion of the stent in expanded condition is then rolled on said coated roll on surface; the stent is then withdrawn from the roll on surface, the solvent is allowed to evaporate, and the elastomeric composition adhered to the stent is polymerized.

A further variant method provides for using a covering layer formed of a tube made of an elastomeric polymerisable composition, inserting the contracted stent into the tube, allowing the contracted stent to expand in the tube and vulcanizing or similarly welding the surface of contact between the stent and the tube.

Still a further variant method also provides for using a covering layer formed of a tube made of an elastomeric polymerisable composition, coating the inside of the tube with an adhesive medium, inserting the contracted stent into the tube, and allowing the stent to expand radially in the so coated tube and the adhesive medium to cure, to thereby achieve adhesion of the assembly of stent and tube.

As a variant of this method, the inside of the tube may be coated with an elastomeric polymerisable composition dissolved in an amount of solvent permitting contact forming, whereby after expansion of the stent, the solvent is allowed to evaporate and the elastomeric coating adhered by contact to the tube and to the stent is polymerized.

In a further variant the covering layer of elastic material may be adhered to the stent by radial pressure of the stent against the covering layer. In that case, the covering layer may be, for instance, formed of a tube made of an elastomeric composition stretched over the stent in order to allow contraction and expansion thereof. Adhesion of the covering layer to the stent will be achieved by surface adhesion forces with additional interpenetration between the covering layer and the stent.

In another variant, also not shown, the covering layer may have a structured surface towards the wall of the stent, whereby adhesion of the covering layer to the stent will be achieved by some engagement of said structured surface into the discontinuous structure of the stent.

Of course, in all these variants, the discontinuous wall of the stent may be covered with the continuous covering layer all over its length or only over a portion thereof.

I claim:

1. A method for applying a covering layer to a stent comprising:

(a) radially contracting the stent;
   (b) coating the inner surface of a tube with a lifting medium;
   (c) inserting at least a portion of the contracted stent into the tube;
   (d) radially expanding at least the portion of the stent in the tube or allowing at least the portion of the stent to radially expand in the tube;
   (e) preparing an elastomeric composition dissolved in a solvent;
   (f) coating the tube and stent with the elastomeric polymerisable composition dissolved in the solvent;
   (g) evaporating the solvent;
   (h) polymerizing the elastomeric composition and forming at least a portion of a layer on the stent in the tube; and
   (i) removing the stent from the tube.

2. A method for applying a covering layer to a stent comprising:

(a) coating a surface with a lifting medium;
   (b) preparing an elastomeric polymerisable composition dissolved in a solvent;
   (c) coating the surface with the elastomeric polymerisable composition dissolved in the solvent;
   (d) rolling at least a portion of the stent, in an expanded condition, on the surface;
   (e) removing the stent from the surface;
   (f) evaporating the solvent from the stent; and
   (g) polymerizing the elastomeric polymerisable composition on at least the portion of the stent.

3. A method for coating a stent comprising:

(a) inserting a radially contracted stent into a tube, the tube having an inner surface and the stent having an inner and outer surface;
   (b) radially expanding the stent or allowing the stent to radially expand in the tube so that at least part of the stent outer surface makes contact with at least part of the tube inner surface;
   (c) coating at least part of the inner and/or the outer surface of the stent with an elastomeric polymerisable composition dissolved in a solvent;
   (d) evaporating the solvent;
   (e) polymerizing the elastomeric composition; and
   (f) removing the coated stent from the tube.

4. A method for coating a stent comprising:

(a) coating a surface with a lifting medium:
   (b) coating the surface with an elastomeric polymerisable composition dissolved in a solvent;
   (c) rolling at least a portion of an expanded stent on the surface to coat at least part of the stent with the elastomeric polymerisable composition comprising a solvent;
   (d) removing the stent from the surface;
   (e) evaporating the solvent; and
   (f) polymerizing the elastomeric composition.

5. A method for applying a covering layer to a stent comprising:

(a) coating the inner surface of a tube with a lifting medium;
   (b) coating the tube with an elastomeric composition dissolved in a solvent and then evaporating the solvent;
   (c) radially contracting a stent;
   (d) inserting at least a portion of the contracted stent into the tube;
   (e) radially expanding at least the portion of the stent in the tube or allowing at least the portion of the stent to radially expand in the tube;
   (f) coating the tube and stent with an elastomeric composition dissolved in a solvent, which may be the same as or different than the elastomeric composition and solvent of step (b), and then evaporating the solvent;
   (g) polymerizing the elastomeric composition and forming at least a portion of a layer on the stent in the tube; and
   (h) removing the stent from the tube.

* * * * *